United States Patent [19]

Tran et al.

[11] Patent Number: 5,416,229

[45] Date of Patent: May 16, 1995

[54] POLYMETHYLALUMINOXANE OF ENHANCED SOLUTION STABILITY

[75] Inventors: Nam H. Tran, Houston; Dennis L. Deavenport, Seabrook, both of Tex.; Dennis B. Malpass, Peekskill, N.Y.; Constance S. Rabbitt, Pasadena, Tex.

[73] Assignee: Akzo Nobel Chemicals Inc., Chicago, Ill.

[21] Appl. No.: 227,836

[22] Filed: Apr. 14, 1994

Related U.S. Application Data

[62] Division of Ser. No. 853,466, Mar. 18, 1992, Pat. No. 5,329,032.

[51] Int. Cl.$^6$ ............................................. C07F 5/06
[52] U.S. Cl. .............................. 556/179; 252/182.35; 252/183.13
[58] Field of Search .................. 556/179; 252/182.35, 252/183.13

[56] References Cited

U.S. PATENT DOCUMENTS

| | | | |
|---|---|---|---|
| 2,744,074 | 5/1956 | Theobold et al. | 260/2 |
| 4,968,827 | 11/1990 | Davis | 556/179 |
| 5,003,095 | 3/1991 | Beard | 556/179 |
| 5,041,584 | 8/1991 | Crapo et al. | 556/179 |
| 5,066,631 | 11/1991 | Sangokoya et al. | 502/152 |
| 5,093,295 | 3/1992 | Tomotsu et al. | 502/152 |
| 5,329,032 | 8/1993 | Sangokoya | 536/179 |

FOREIGN PATENT DOCUMENTS

| | | | |
|---|---|---|---|
| 372617 | 6/1990 | European Pat. Off. | C07F 5/06 |
| 393358 | 10/1990 | European Pat. Off. | C07F 5/06 |
| 149949 | 9/1983 | Japan | C08L 85/00 |
| 271295 | 12/1991 | Japan | C07F 5/06 |
| 49293 | 2/1992 | Japan | C07F 5/06 |

*Primary Examiner*—Arthur C. Prescott
*Attorney, Agent, or Firm*—Richard P. Fennelly; Louis A. Morris

[57] ABSTRACT

Polymethylaluminoxane compositions having increased solution stability in organic solvent and, in some cases, increased polymerization activity, which comprise moieties derived from an organic compound containing an electron-rich heteroatom (e.g., from Group V and/or Group VI of the Periodic Table) and a hydrocarbyl moiety. These compositions can be formed by reaction of trimethylaluminum, the organic compound, and water. They can also be formed by reaction of pre-formed polymethylaluminoxane the organic compound, which can be a hydrocarbyl group-containing compound containing an electron-rich heteroatom (e.g., oxygen, nitrogen, or sulfur), either with or without an active hydrogen atom connected to the heteroatom. The organic compound, in some embodiments, has also been found to be effective in increasing the catalytic activity of modified polymethylaluminoxane which, in addition to methyl, contain $C_2$ and higher alkyl groups for enhanced solution stability.

9 Claims, No Drawings

POLYMETHYLALUMINOXANE OF ENHANCED SOLUTION STABILITY

This is a division of application Ser. No. 07/853,466 filed Mar. 18, 1992, now U.S. Pat. No. 5,329,032.

BACKGROUND OF THE INVENTION

Polymethylaluminoxane, which is traditionally formed from the reaction of trimethylaluminum and a source of water, is used as a catalyst component with a metallocene catalyst component in olefin polymerizations. As indicated in European Patent Publication No. 393,358, it is difficult to form homogeneous polymethylaluminoxane solutions having good storage stability due to precipitation or gel formation in such solutions upon storage. This European patent publication mentions the reaction of polymethylaluminoxane with a $C_3$ to $C_9$ branched alkylaluminum compound in organic solvent to yield a homogeneous solution. A representative alkylaluminum compound which can be used is triisobutylaluminum.

An earlier disclosure of modified polymethylaluminoxane containing $C_2$ or higher alkyl groups, which has enhanced solubility in organic solvent is European Patent Publication No. 372,617 which describes compositions containing certain alkyl groups, e.g., isobutyl, n-butyl and n-hexyl groups. This earlier European patent publication (which corresponds to U.S. Pat. No. 5,041,584) does not specifically address the issue of enhancing the storage stability of conventional polymethylaluminoxane solutions which are not so modified.

A more recent U.S. patent which describes the use of tri-n-alkylaluminum compounds, having from 2 to 20 carbon atoms in the alkyl groups, to aid in the solubilization of polymethylaluminoxane in hydrocarbon solvent is U.S. Pat. No. 5,066,631 to S. A. Sangokoya.

All of the above references focus upon the use of organoaluminum compounds as either reagents or additives to yield homogeneous polymethylaluminoxane solutions.

SUMMARY OF THE INVENTION

The present invention, in one embodiment, is a novel, polymethylaluminoxane, having enhanced solution stability against precipitation or gelation during storage and, in some cases, enhanced polymerization activity. Another embodiment of the present invention relates to the improvement of the catalytic activity of certain modified polymethylaluminoxane compositions (of the type disclosed in U.S. Pat. No. 5,041,584), which can already possess good solubility and solution stability due to the presence of a sufficiently high level of $C_2$ or higher alkyl groups, by using certain of the additives, to be described in greater detail below, which are useful in enhancing the solution stability of conventional polymethylaluminoxane.

A polymethylaluminoxane composition in accordance with this invention, is formed by the use, as either an original reagent or as a later additive, of an organic compound containing an electron-rich heteroatom and hydrocarbyl substituents to achieve the enhanced solution stability characteristics and, in some cases, enhanced activity in olefin polymerization for the polymethylaluminoxane which results. Representative compounds which contain these features include organic hydrocarbyl compounds containing electron-rich heteroatoms with active hydrogen atoms and organic hydrocarbyl compounds containing electron-rich heteroatoms without the additional presence of active hydrogen atoms. The polymethylaluminoxane composition of the present invention can be formed, for example: (1) by originally reacting and/or complexing trimethylaluminum, the compound containing the electron-rich heteroatom and the selected hydrocarbyl moiety or moieties, and water as reagents; or (2) by combining the compound containing the electron-rich heteroatom and the hydrocarbyl moiety or moieties with a pre-formed polymethylaluminoxane. Modified polymethylaluminoxane of the type described in U.S. Pat. No. 5,041,584, where a portion of the methyl groups in conventional polymethylaluminoxane are replaced by higher alkyl groups, is intended to be embraced by the term "polymethylaluminoxane" as used herein to the extent that the proportion and/or nature of the higher alkyl groups (i.e, the $C_2$ or higher alkyl groups) is not sufficient to confer the desired degree of solution stability on the entire system.

In its broadest sense, the present invention relates to a polymethylaluminoxane which contains moieties derived from the aforementioned compound, namely, an electron-rich heteroatom and a hydrocarbyl group or groups.

DETAILED DESCRIPTION OF THE INVENTION

Conventional, unmodified polymethylaluminoxane comprises or contains the recurring unit

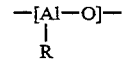

where R is methyl, as one of the principal and essential repeating units. This material has well-recognized post-precipitation problems in organic solvent media upon storage, as previously described. It is formed by reacting trimethylaluminum with a source of water. Many specialized techniques for doing so are known to persons of ordinary skill in the art. U.S. Pat. No. 5,041,585 to D. L. Deavenport et al. describes an especially preferred means for reacting trimethylaluminum with an atomized spray of water and is incorporated herein by reference, as illustrating such a preferred technique. The use of an aluminoxane reaction moderator, i.e., a preformed polymethylaluminoxane, for use in such a procedure is described in U.S. Ser. No. 712,310, filed Jun. 7, 1991, which is also incorporated herein by reference.

In accordance with the present invention, more enhanced organic solvent solubility characteristics, with a concomitant reduction of post-precipitation or gelation problems, and, in some cases, enhanced polymerization activity, can be achieved for such polymethylaluminoxane compositions by utilization of a certain type of organic compound, as either a reagent in forming the polymethylaluminoxane or as an additive to a previously formed polymethylaluminoxane. The organic compound which has been found to be useful in accordance with the present invention has two essential features. The first is at least one electron-rich heteroatom (e.g., containing one or more unshared electron pair(s)), such as one or more heteroatoms from Groups V and/or VI of the Periodic Table of the Elements, such as oxygen, nitrogen, phosphorus and/or sulfur. In many cases, the compound will also have an active hydrogen atom attached to the heteroatom as in the case of alcohols and thiols, but this is not essential since trialkyl amines and dialkyl ethers, which lack an active hydrogen atom but which have an electron-rich nitrogen or oxygen atom, are effective. The second feature is hydrocarbyl substitution which will generally be, in the aggregate with the combination of the carbon/hydrogen content of the molecule, sufficiently large to give the requisite degree of solubility for the polymethylaluminoxane. Representative hydrocarbyl groups include alkyl of, for example, $C_4$ or higher, aryl, alkaryl, and aralkyl. In the case of certain compounds, however, such as trialkyl amines or dialkyl ethers, the individual hydrocarbyl groups can be of lesser molecular weight than the foregoing, representative hydrocarbyl groups even though their aggregate total may be within that range.

Generally, the amount of electron-rich heteroatom-containing compound to be utilized in accordance with the invention will be present at up to about 15 mole %, based on the weight of polymethylaluminoxane present or to be formed, in a preferred embodiment, although higher amounts can be used to achieve solution stability. In the latter cases, however, reduction in the catalytic activity of the treated polymethylaluminoxane is sometimes observed. Generally speaking, the person of ordinary skill in the art will probably select a level of from about 0.1 mole % to about 10 mole %, based on the amount of polymethylaluminoxane present or to be formed in order to achieve the best balance of solution stability and catalytic activity.

One way to practice the invention is to include the selected amount of the compound, containing the electron-rich heteroatom(s) and hydrocarbyl group(s), with the trimethylaluminum-containing reagent, normally employed to synthesize the polymethylaluminoxane (and, optionally, a preformed polymethylaluminoxane reaction moderator), followed by reaction of the resulting mixture with water to form a polymethylaluminoxane product. Alternatively, the compound can be placed in an appropriate hydrocarbon solvent to which the trimethylaluminum-containing reagent and water are thereafter added either simultaneously or in sequence. In both of these embodiments, the compound, which is used in accordance with the present invention, is added during the process of forming the polymethylaluminoxane and is thereby incorporated in the final solubilized polymethylaluminoxane which is formed in solubilized form in the solvent.

If desired, the compound can alternatively be added to a hydrocarbon solvent containing a pre-formed, solubilized polymethylaluminoxane with, for example, heating to achieve the desired degree of interaction and thereby achieve the results intended for the present invention.

While the precise manner in which the electron-rich heteroatom-containing, hydrocarbyl group-containing compound functions to achieve the positive effect of the present invention is not known, it is believed that such a compound may somehow either react with or coordinate with the polymethylaluminoxane or free trimethylaluminum by virtue of the electron-rich nature of the heteroatom. This coordination/reaction might prevent undesired coordination between adjacent polymethylaluminoxane chains or oligomeric/polymeric structures, which would normally occur in the absence of the compound, leading to decreased solubility of such resulting materials in organic solvent solution. Alternatively, addition of the compound containing the electron-rich heteroatom may impart enhanced solution stability by interacting primarily with free trimethylaluminum in the solution to reduce its reactivity thereby interfering with the aging reaction between free trimethylaluminum and polymethylaluminoxane. These explanations are set forth as a possible theory of operation, and there is no intention on the part of the present inventors to be bound by such a theory merely because it is given as a potential explanation for the results observed.

As indicated earlier, it is within the purview of the present invention to use compounds containing heteroatoms, such as those from Groups V and VI of the Periodic Table of the Elements, which are capable of donating electrons (i.e., a so-called electron-rich site) to the electron deficient aluminum atoms of the polymethylaluminoxane in solution to, presumably, form complexes or reaction products which result in increased solution stability for the resulting product.

One class of compound for use herein are compounds containing the electron-rich heteroatom site and at least one active hydrogen atom. Yet another class of useful compounds are those containing the previously described heteroatom which do not contain an active hydrogen atom. Non-limiting examples of such reagents containing such a hydrogen atom include compounds having the following general structures (where R is the selected hydrocarbyl group): $ROH$; $RCO_2H$; $RNH_2$; $R_2NH$; $RSH$; $RCONH_2$; $RCONHR$; $RN(CH_2CH_2OH)_2$; $R_2NCH_2CH_2OH$; $RC(O)NHCH_2CH_2OH$; $RC(S)OH$; and $R_2PO_2H$. Other compounds for use include, as representative examples, compounds containing an electron-rich heteroatom which do not contain an active hydrogen atom and which are of the following general formulae: $RCONR_2$; $RSR$; $ROR$; $RC(O)OR$; $RC(O)R$; $RC(S)R$; and $RC(O)H$, where R is as defined above. An especially preferred R group is higher alkyl ($C_4$ or higher) which is optionally branched at the $\beta$ carbon or a carbon further removed from the $\alpha$ carbon atom. The preferred mode of addition is to react the active hydrogen containing hydrocarbyl moiety with preformed polymethylaluminoxane. However, incorporation into the final product can also be achieved by adding the modifier to the trimethylaluminum-containing reagent in a suitable solvent followed by addition of water, or by adding the compound to the solvent before water and trimethylaluminum-containing reagent are added, to produce the stabilized polymethylaluminoxane/solvent composition.

Examples of such electron donor compounds, which form one type of effective compound for use herein, include the trihydrocarbyl amines, e.g., tri-n-octylamine, the trihydrocarbylphosphines, e.g., triphenylphosphine, and the dihydrocarbyl ethers, e.g., diphenylether. Ethers and amines with $C_4$ or higher alkyl groups are a preferred class of compounds to use. Two particular compounds of this general type which are particularly preferred from the standpoints of performance, availability, and cost are tridodecylamine and dibutylether.

A variety of general factors can be used to assist in the selection of particular, appropriate electron-rich heteroatom-containing and hydrocarbyl group-containing compound:

(1) If substituents are present on the backbone or nucleus of the selected compound, they should not give rise to an undue amount of steric hindrance in the vicinity of those portions of the compound (namely, the heteroatom or heteroatoms) which are believed to coordinate or react with the preformed aluminoxane or in forming the desired aluminoxane.

(2) The use of multifunctional reagents in which the various functional groups are capable of reacting with, or in forming, more than one methylaluminoxane molecule so as to lead to bridged, or ultrahigh molecular weight species which readily precipitate are also not deemed to be preferred.

(3) Solution stability shows increase as the hydrocarbyl group increases in size and molecular weight. For example, methanol, when used as the alcohol reagent, yields either no stability enhancement or poor stability enhancement beyond four days, whereas dodecanol imparts stability for fourteen days under the test procedure to be described below. Alcohols of intermediate size imparts stability enhancements which are intermediate in scope: 2-ethyl-1-butanol (nine days); and 1-hexanol (seven days).

(4) There is a concentration factor. With paranonylphenol for example, the stability was observed to increase as the molar percent was raised, e.g., at 0.1, 0.5, 1.0, 5.0 and 10.0 mole % levels, respectively. Post-precipitation was observed within a few days with 0.1 and 0.5 mole % levels using an accelerated aging test protocol. The 1.0 mole % level lasted for several weeks before noticeable precipitation was observed. The 5.0 and 10.0 mole % concentrations showed no tendency to post-precipitate.

It is deemed that modified polymethylaluminoxane of the type shown in U.S. Pat. No. 5,041,584 will not have the degree of poor storage stability experienced by conventional polymethylaluminoxane, particularly if the type and/or quantity of higher alkyl groups therein is adequate to achieve such solution stability. Even though one embodiment of the present invention, i.e., enhanced solution stability is not as much in need of achievement with such modified compositions, it has unexpectedly been found that the catalytic activity of such a modified polymethylaluminoxane can nevertheless be increased by use of certain of the compounds described herein, e.g., the trialkylamines and the dialkyl ethers which are used with conventional polymethylaluminoxane for improved solution stability as well.

The present invention is further illustrated by the Examples which follow.

EXAMPLE 1

Procedure for Testing Stability

Candidates for use as a stabilizer in solutions of polymethylaluminoxane (PMAO) in toluene were tested using a test protocol which, for convenience, would accelerate the potential gelation or precipitation phenomenon normally observed with polymethylaluminoxane-solvent compositions over the period of many weeks to several months, depending upon the ambient temperature during storage. For example, PMAO solutions with aluminum concentrations of 10%–11% will normally show storage stabilities, before gelation/precipitation is noted, of less than about three months when stored in steel containers exposed to outside ambient temperatures in Texas. The PMAO was formed by use of the water aspiration technique described in U.S. Pat. No. 5,041,585. Initial testing was conducted to verify the effectiveness of a variety of potential stabilizers. This involved addition of 1 mole % concentrations (molar ratio of additive/Al concentration in PMAO=1:100) of the chemical to PMAO/toluene which contained 10 wt % soluble aluminum. This blend of material was transferred to a 50 ml Wheaton ® vial and recapped with a Teflon ® coated liner (to prevent interaction of toluene with rubber liner) under a nitrogen atmosphere in a dry box. The vial was placed in an oil bath maintained at 50°–55° C. The vial contents were observed on a daily basis for changes in appearance and documented appropriately. Experiments were terminated after thirty days. Substrates that inhibited or substantially reduced solids formation under these conditions were subjected to additional testing. In the above tests, controls were run against a majority of the compounds tested in the same experiment. All controls showed gel or solids formation at four days or sooner.

Further experimentation was conducted to determine optimum concentrations of potential stabilizers. Varying mole % concentrations of the substrate were tested using the procedure previously described. These vials were observed on a daily basis and sampled at two week intervals to determine the aluminum content. At the end of the thirty day period the results were evaluated.

Table 1 lists the results in stability testing of substrates for PMAO/toluene. PMAO/toluene from the same lot was used for all testing. Both initial and final aluminum values were determined in most cases. The percent soluble aluminum loss after the thirty day heating period was also reported for a majority of the runs.

TABLE 1

| | Stability Testing of Substrates for PMAO/Toluene | | | | |
| Substrate | Soluble Aluminum in PMAO/Toluene with Substrate (Wt %) | Substrate (Mole %) | First Solids/Gel Formation Observed (Days) | Aluminum PMAO/Toluene After 30 Days (Wt %) | Aluminum Loss (%) |
| --- | --- | --- | --- | --- | --- |
| Control | 10.0 | 0 | 4 | 8.0 | 20.0 |
| Control | 9.8 | 0 | 4 | 7.8 | 20.4 |
| Control | 9.8 | 0 | 4 | 7.8 | 20.4 |
| Control | 9.8 | 0 | 4 | 8.8 | 10.2 |
| Control | 9.8 | 0 | 4 | 8.3 | 15.3 |
| Control | 9.6 | 0 | 3 | 8.2 | 14.6 |
| Control | 9.5 | 0 | 4 | — | — |
| ALCOHOLS | | | | | |
| Methanol | 10.0 | 1 | 4 | 8.9 | 11.0 |
| Ethanol | 10.0 | 1 | 4 | 8.7 | 13.0 |

TABLE 1-continued

| Propanol | 10.0 | 1 | 4 | 8.6 | 14.0 |
|---|---|---|---|---|---|
| Butanol | 10.0 | 1 | 7 | 9.1 | 9.0 |
| Hexanol | 10.0 | 1 | 12 | 9.6 | 4.0 |
| Octanol | 10.0 | 1 | 12 | 9.6 | 4.0 |
| Decanol | 10.0 | 1 | 13 | 9.5 | 5.0 |
| Dodecanol | 9.8 | 1 | 14 | 9.2 | 6.1 |
| Dodecanol | 9.8 | 3 | 30 | 9.6 | 2.0 |
| Dodecanol | 9.8 | 5 | 30 | 9.5 | 3.1 |
| t-Butyl alcohol | 9.8 | 1 | 6 | 8.9 | 9.2 |
| t-Pentyl alcohol | 10.0 | 1 | 4 | 8.3 | 17.0 |
| 2-Ethoxyethanol | 10.0 | 1 | 8 | 9.0 | 10.0 |
| Cyclohexanol | 10.0 | 1 | 5 | 8.6 | 14.0 |
| 2,2-Dimethyl-3-pentanol | 9.8 | 1 | 6 | 8.8 | 10.2 |
| 2,3-Dimethyl-3-pentanol | 9.8 | 1 | 6 | 8.9 | 9.2 |
| 2,4-Dimethyl-3-pentanol | 9.8 | 1 | 6 | 8.8 | 10.2 |
| 2-Ethyl-1-butanol | 9.8 | 1 | 9 | 9.3 | 5.1 |

Stability Testing of Substrates for PMAO/Toluene @ 50° C.

| Substrate | Soluble Aluminum in PMAO/Toluene with Substrate (Wt %) | Substrate (Mole %) | First Solids/Gel Formation Observed (Days) | Aluminum PMAO/Toluene After 30 Days (Wt %) | Aluminum Loss (%) |
|---|---|---|---|---|---|
| Benzyl alcohol | 10.0 | 1 | 4 | 8.0 | 20.0 |
| Nonylphenol | 9.8 | 1 | 13 | 9.7 | 1.0 |
| Nonylphenol | 9.8 | 3 | 30 | 9.5 | 3.1 |
| Nonylphenol | 9.8 | 5 | 30 | 9.5 | 3.1 |
| Nonylphenol | 9.1 | 10 | 26 | 9.0 | 1.1 |
| Butylated hydroxy toluene (BHT) | 9.8 | 1 | 6 | 7.9 | 19.4 |
| Phenethyl alcohol | 10.0 | 1 | immediate | 8.0 | 20.0 |
| 4-Nitrophenol | 9.8 | 1 | immediate | discontinued | — |
| 1,1-Diphenylethanol | 9.5 | 1 | 4 | 7.9 | 16.8 |
| Triethylene glycol monobutyl ether | 9.8 | 1 | immediate | 5.8 | 40.8 |
| 4-Methoxyphenol | 9.6 | 1 | 1 | 6.2 | 35.4 |
| IRGANOX 1076 brand[1] | 9.6 | 1 | 14 | 9.3 | 3.1 |
| THIOL | | | | | |
| 1-Octanethiol | 9.8 | 1 | 13 | 8.9 | 9.2 |
| SILANOL | | | | | |
| Triethylsilanol | 9.8 | 1 | 4 | 8.1 | 17.4 |
| DIOL | | | | | |
| 1,6-Hexanediol | 9.8 | 1 | immediate | 6.4 | 34.7 |
| ESTERS | | | | | |
| Ethylbenzoate | 10.0 | 1 | 5 | 8.0 | 20.0 |
| Dodecylacetate | 9.5 | 1 | 19 | — | — |
| KETONE | | | | | |
| Acetophenone | 10.0 | 1 | 4 | 7.7 | 23.0 |
| ALDEHYDE | | | | | |
| Decyl aldehyde | 9.8 | 1 | 5 | 8.5 | 13.3 |
| PHOSPHINIC ACIDS | | | | | |
| Phenylphosphinic acid | 9.8 | 1 | 22 | 9.7 | 1.0 |
| Diphenylphosphinic acid | 9.8 | 1 | 20 | 9.8 | 0.0 |
| ACIDS | | | | | |
| Benzoic acid | 9.6 | 1 | 5 | 8.1 | 15.6 |
| 2-Bibenzylcarboxylic acid | 9.2 | 1 | 11 | 8.4 | 8.7 |
| Oleic acid | 10.0 | 1 | 5 | 8.2 | 18.0 |
| PRIMARY AMINES | | | | | |
| Octylamine | 9.6 | 1 | 8 | 9.1 | 5.2 |
| Decylamine | 9.8 | 1 | 14 | 9.6 | 2.0 |
| Decylamine | 9.8 | 3 | 30 | 9.7 | 1.0 |
| Decylamine | 9.8 | 5 | 30 | 9.6 | 2.0 |
| 3,3-Diphenylpropylamine | 9.8 | 1 | 15 | 9.6 | 2.0 |
| SECONDARY AMINES | | | | | |
| Dibutylamine | 9.8 | 1 | 11 | 8.8 | 10.2 |
| Dioctylamine | 9.6 | 1 | 20 | 9.3 | 3.1 |
| Dicyclohexylamine | 9.8 | 1 | 28 | 9.7 | 1.0 |
| Diphenylamine | 9.6 | 1 | 3 | 8.4 | 12.5 |
| 2,2-Dipyridylamine | 9.5 | 1 | 15 | 9.2 | 3.2 |
| TERTIARY AMINES | | | | | |
| Triethylamine | 9.6 | 1 | 6 | 8.9 | 7.3 |
| N,N-Diethylcyclohexylamine | 9.5 | 1 | over 30 | 9.5 | 0.0 |
| Tributylamine | 9.5 | 1 | over 23 | — | — |
| Trihexylamine | 9.5 | 1 | over 23 | — | — |
| Tri-n-octylamine | 9.6 | 0.1 | 13 | 9.0 | 6.3 |
| Tri-n-octylamine | 9.6 | 0.3 | over | 9.3 | 3.1 |

TABLE 1-continued

| | | | | | |
|---|---|---|---|---|---|
| Tri-n-octylamine | 9.6 | 0.5 | 30 over | 9.5 | 1.0 |
| Tri-n-octylamine | 9.8 | 1 | over 30 | 9.8 | 0.0 |
| Tri-n-octylamine | 9.4 | 5 | over 30 | 9.4 | 0.0 |
| Tridodecylamine (ARMEEN 312) | 9.5 | 0.5 | over 23 | — | — |
| Tridodecylamine (ARMEEN 312) | 9.5 | 0.75 | over 23 | — | — |
| Tridodecylamine (ARMEEN 312) | 9.5 | 1 | over 23 | — | — |
| Trihexadecylamine (ARMEEN 316) | 9.5 | 1 | 19 | — | — |
| Quinuclidine | 9.6 | 1 | 14 | 9.0 | 6.3 |
| N,N-Diethylaniline | 9.6 | 1 | 15 | 9.6 | 0.0 |
| Triphenylamine | 9.6 | 1 | 6 | 8.1 | 15.6 |
| Pyridine | 9.6 | 1 | 6 | 8.8 | 8.3 |
| ETHOXYLATED AMINES | | | | | |
| ARMOSTAT 310 brand[2] | 9.5 | 1 | 21 | — | — |
| ARMOSTAT 410 brand[3] | 9.5 | 1 | over 23 | — | — |
| ARMOSTAT 710 brand[4] | 9.5 | 1 | over 23 | — | — |
| ARMOSTAT 1800 brand[5] | 9.5 | 1 | over 23 | — | — |
| ETHERS | | | | | |
| Dibutylether | 9.8 | 1 | 29 | 9.6 | 2.0 |
| Diphenylether | 9.8 | 1 | 26 | 9.6 | 2.0 |
| PHOSPHINE | | | | | |
| Triethylphosphine | 9.6 | 1 | 6 | 8.7 | 9.4 |

[1] octadecyl 3-(3,5-di-tert-butyl-4-hydroxy-phenyl)-propionate.
[2] N,N-bis(2-hydroxyethyl) $C_{18}$—$C_{18}$ alkyl amine having a 50/50 ratio of saturated to unsaturated groups.
[3] N,N-bis(2-hydroxyethyl) $C_8$—$C_{14}$ alkyl amine.
[4] N,N-bis(2-hydroxyethyl) $C_{16}$—$C_{18}$ alkyl amine, containing mainly unsaturated alkyl groups.
[5] predominantly saturated stearyl amine.

EXAMPLE 2

Ethylene Polymerization Procedure

A one liter stainless steel autoclave was heated to 100° C. for one hour to remove moisture and then placed under a nitrogen purge while cooling. The autoclave was then pressurized (45 psig) with ethylene and vented twice. The autoclave was then filled with 500 cc of anhydrous, high purity toluene from Aldrich Chemical Co., was pressurized with ethylene and was heated to 80° C. The ethylene was then vented, and the system was repressurized and vented. At this point, aluminoxane/toluene/stabilizer solution (containing $4 \times 10^{-3}$ moles Al) was added by syringe. After about one minute of stirring, a freshly prepared solution containing $1 \times 10^{-7}$ moles of zirconocene dichloride ($Cp_2ZrCl_2$) in toluene was added. The system was then pressurized to 45 psig with ethylene and the polymerization was conducted at 80° C. for fifteen minutes. The polymerization was terminated by venting the ethylene. The polymer was dried to constant weight and an activity value was calculated on the basis of gPE/(gZr.atm.hr). Table 2 shows the ethylene polymerization activities of PMAO/toluene solutions containing certain substrates, respectively:

TABLE 2

| Substrate | Mole % | Activity ($10^6$ g PE/ g Zr · atm · hr) | % Gain or (% Decrease) |
|---|---|---|---|
| Control | 0 | 1.66 | 0 |
| Nonylphenol | 1 | 1.72 | 4 |
| Nonylphenol | 3 | 1.60 | (4) |
| Nonylphenol | 5 | 1.23 | (26) |
| Nonylphenol | 10 | 0.64 | (61) |
| Dodecanol | 1 | 1.52 | (8) |
| Dodecanol | 3 | 1.05 | (37) |
| Dodecanol | 5 | 0.88 | (47) |
| IRGANOX 1076 brand | 1 | 1.45 | (13) |
| Decylamine | 1 | 1.71 | 3 |
| Decylamine | 3 | 1.35 | (19) |
| Decylamine | 5 | 0.85 | (49) |
| Dibutylether | 1 | 2.12 | 28* |
| Dioctylether | 1 | 1.78 | 7 |
| Diphenylether | 1 | 1.68 | 1 |
| Dioctylsulfide | 1 | 1.78 | 7 |
| Octylamine | 1 | 1.58 | (5) |
| Dioctylamine | 1 | 1.94 | 17* |
| Triethylamine | 1 | 1.53 | (8) |
| Diphenylphosphinic acid | 1 | 1.18 | (29) |
| Tri-n-octylamine | 1 | 2.39 | 44* |
| Tri-n-octylamine | 5 | 1.93 | 16* |
| Quinuclidine | 1 | 1.72 | 4 |
| Quinuclidine | 3 | 0.67 | (60) |
| ALIQUAT brand | 1 | 0.19 | (89) |
| Triethylphosphine | 1 | 0.85 | (49) |
| Diphenylphosphinic acid | 1 | 1.18 | (29) |
| ARMOSTAT 410 brand | 1 | 1.78 | 7 |
| ARMOSTAT 710 brand | 1 | 2.06 | 24* |
| ARMOSTAT 1800 brand | 1 | 1.61 | (3) |
| Dibutylether** | 1 | 1.66 | 0 |
| ARMEEN 312 brand | 0.75 | 2.03 | 22* |
| ARMEEN 312 brand | 1 | 2.15 | 30* |

*particularly preferred % gains were achieved.
**substrate was introduced during the production of the PMAO/toluene composition.

EXAMPLE 3

Three test substrates were added to PMAO in toluene at a molar ratio of 1:100 substrate to aluminum. Ethylene polymerization tests were conducted at several different stages of aging using the procedure described in Example 2. All aging times are at room temperature unless otherwise indicated. The identity of the tested substrate is The results of the polymerization activities are given in Table 3:

TABLE 3

| Aging Conditions | Polymer. Activity ($10^6$ PE/g Zr · atm · hr) | % Gain or (Decrease) |
|---|---|---|
| No Substrate (Control) | | |
| None | 1.66 | — |
| Trioctylamine Substrate | | |
| 0 Days | 2.16 | 30 |
| 3 Days | 3.16 | 90 |
| 5 Days | 3.19 | 92 |
| 60 Days* | 3.34 | 101 |
| Dioctylamine Substrate | | |
| 0 Days | 1.58 | (5) |
| 9 Days at 50° C. | 2.45 | 48 |
| Dioctylether Substrate | | |
| 0 Days | 1.78 | 7 |
| 6 Days | 2.79 | 68 |

*30 days at 50° C. followed by 30 days at ambient.

EXAMPLE 4

Two ethylene polymerization tests were conducted using the procedure of Example 2 except that the test conditions were 40° C. and one atmosphere ethylene. The cocatalyst used in the tests was a modified polymethylaluminoxane-heptane solution which is described in U.S. Pat. No. 5,041,584. The difference in the two tests is the presence in the second of trioctylamine at a molar ratio of 1:100 (amine to aluminum). The following results were obtained:

TABLE 4

| Amine Present (Mole %) | Polymerization Activity ($10^5$ g PE/g Zr.atm.hr) | % Gain or (Decrease) |
|---|---|---|
| 0 | 2.9 | — |
| 1.0 | 5.4 | 86 |

The foregoing Examples are intended to merely illustrate certain embodiments of the present invention and, for that reason, should not be construed in a limiting sense. The scope of protection sought is set forth in the claims which follow.

We claim:

1. A modified polymethylaluminoxane composition, which comprises, in addition to methyl groups, hydrocarbyl groups higher in molecular weight than methyl for enhanced solvent solubility, which modified polymethylaluminoxane is normally stabilized against precipitation from organic solvent over time and which is dissolved in organic solvent, said polymethylaluminoxane comprising moieties derived from a organic compound containing at least one electron-rich heteroatom and at least one hydrocarbyl group, the presence of such moieties from that organic compound being effective to enhance the catalytic activity of the modified polymethylaluminoxane composition.

2. A composition as claimed in claim 1 wherein the heteroatom is selected from the group consisting of Group V and Group VI of the Periodic Table of the Elements.

3. A composition as claimed in claim 1 wherein the heteroatom is selected from the group consisting of oxygen, nitrogen, phosphorus, and sulfur.

4. A composition as claimed in claim 1 wherein the organic compound comprises an electron-rich heteroatom and an active hydrogen atom.

5. A composition as claimed in claim 1 wherein the organic compound comprises an electron-rich heteroatom and no active hydrogen atom.

6. A composition as claimed in claim 1 wherein organic compound is an ether.

7. A composition as claimed in claim 1 wherein the organic compound is an amine.

8. A composition as claimed in claim 6 wherein the organic compound is dibutyl ether.

9. A composition as claimed in claim 7 wherein the organic compound is tridodecyl amine.

* * * * *